United States Patent
Shih et al.

(10) Patent No.: US 6,344,433 B1
(45) Date of Patent: Feb. 5, 2002

(54) LONG-ACTING DISINFECTANT AND ITS PREPARATION METHOD

(76) Inventors: Ying-Chi Shih, 3F-1, No. 342, Changan West Road, Taipei; Xiu-Ping Wang, No. 153, Naniau West Street, Yuts City Shan Shi Province, both of (TW)

(*) Notice: Subject to any disclaimer, the term of this patent is extended or adjusted under 35 U.S.C. 154(b) by 13 days.

(21) Appl. No.: 09/611,561

(22) Filed: Jul. 7, 2000

(30) Foreign Application Priority Data

Dec. 30, 1999 (TW) ......................................... 99127317 A

(51) Int. Cl.$^7$ .............................. C11D 1/72; C11D 3/48; C11D 3/30
(52) U.S. Cl. ...................... 510/386; 510/388; 510/499; 510/506; 424/404
(58) Field of Search ................................. 510/386, 388, 510/499, 506; 424/404

(56) References Cited

U.S. PATENT DOCUMENTS

| | | | | |
|---|---|---|---|---|
| 5,653,970 A | * | 8/1997 | Vermeer | 424/70.24 |
| 5,948,416 A | * | 9/1999 | Wagner et al. | 424/401 |
| 6,107,263 A | * | 8/2000 | D'Ambrogio et al. | 510/237 |
| 6,214,783 B1 | * | 4/2001 | Gambogi et al. | 510/237 |
| 6,258,763 B1 | * | 7/2001 | Arvanitidou et al. | 510/221 |

* cited by examiner

*Primary Examiner*—Gregory Delcotto
(74) *Attorney, Agent, or Firm*—Bacon & Thomas

(57) ABSTRACT

This invention is with regard to a kind of Long-acting disinfectant. Its ingredients are composed of 2,4,4'-trichloro-2'-Hydroxy diphenyl ether, amino emulsified-silica resin, 1,2 propanediol, fatty alcohol polyethenoxy ether and distilled water. First, the fatty alcohol polyethenoxy ether should be mixed with distilled water, 2,4,4'-trichloro-2'-hydroxy diphenyl ether is to be put into a high speed agitator, to make the mixture in the agitator dissolved by stirring at the temperature of 50~70° C. When the temperature has been lowed down, the amino-silica-milk resin should be added.

After stirring in the agitator at low revolution speed for several minutes, provided the mixture is homogeneous, the end product can be obtained. The long-acting disinfectant has the specific properties of excellent disinfecting effect, long-acting potency, repeated-pollution resistant, non-toxic & safe etc. Its antiseptic rate at surface and bacteriostasis after two years storage, could still be up to 66%.

4 Claims, No Drawings

LONG-ACTING DISINFECTANT AND ITS PREPARATION METHOD

FIELD OF THE INVENTION

The invention concerns the aspect of disinfection, especially the long-acting disinfectant, suitable to prolong disinfecting of circulating bank notes and food packing paper, as well as their preparation.

BACKGROUND OF THE INVENTION

As is commonly known sanitation and harm caused by circulating bank notes is a difficult point drawing wide attention in today's world. But there is no scientific and effective solution will now.

When circulating bank notes or other paper products are to be disinfected the choice and requirements of the disinfectant are critical. It requires that the disinfectant would not only be bacteriostasis capable, but also anti-septic. At the same time, long-acting effect is even more a special and important requirement. The disinfectant with short lasting effect and single bacteriostasis, is not practical. Although many disinfectants are in the market, only a few disinfectants possess simultaneously the specifications of bacteriostasis, long-acting disinfection and safety.

As is commonly known, 2,4,4'-trichloro-2'-hydroxy diphenyl ether(HD244) is a very stable and safe disinfectant. But owing to its being in crystal powder shape, hardly soluble in water, is usually is made into aqueous emulsion disinfectant. But it usually is limited to bacteriostasis, and its disinfection is hampered by emulsifying agent. This is also reported in Japanese Patent JP60-90564, JP59-64172, JP50-100766 and Chinese Patent CN1041018A.

In addition, The organic-silicon quaternary ammonium salt long-acting disinfectant, (DC-5700) produced by doukonin (USA) co. has a better bacteriostasis than HD244. But according to the classification of Sterilization science and Pharmacogynamics, DC-5700 is a less effective disinfectant and its bacteriostasis is limited in scope.

SUMMARY OF THE INVENTION

The object of the invention is to provide a highly stable long-action, broad-spectrum disinfection, highly effective, safe and nontoxic disinfectant. In order to suit the needs of sanitation treatment of circulating bank notes and paper products for long-acting bacteriostasis and disinfectction, but not impair their physical property or appearance.

Another object of the invention is to provide a preparation method of above-mentioned long-acting disinfectant.

DETAILED DESCRIPTION OF THE INVENTION

The ingredients of the invention are 2,4,4'-trichloro-2'hydroxy diphenyl ether, amino emulsified-silica resin, 1,2 propanediol, fatty alcohol polyethenoxy ether and distilled water. Their mass proportions are as follows:

| | |
|---|---|
| 2,4,4'-trichloro-2'-hydroxy diphenyl ether | 20~50 parts |
| Amino emulsified-silica resin | 3~10 parts |
| 1,2 propanediol | 20~30 parts |
| Fatty alcohol polyethenoxy ether | 10~30 parts |
| Distilled water | 10~40 parts |

The amino emulsified-silica resin is commercially known as TSA202 organic silicon resin.

The above mentioned distilled water may be sterilized.

The preparation method of this long-acting disinfectant is as follows:

Mix fatty alcohol polyethenoxy ether with distilled water in the proportion of 1:1, stir it for 1~3 minutes in a high speed homogenizer of 11,000~19,000 r.p.m. and add 2,4,4'-trichloro-2'-hydroxy diphenyl ether. Adjust the speed of homogenizer to 700~900 r.p.m; stir it for 3~5 minutes at 50~70° C. After it fuses, reduce temperature down to 15~25° C., and amino emulsified-silica resin, then stir it for 2~6 minutes at 200~500 r.p.m.

The process above may also include an additional step of diluting 40 Wt % fortified disinfectant of hydroxy amino diphenyl ether to 0.5~1.3 Wt % with distilled water, which can be used as a surface disinfectant for bank notes or other paper materials.

The characteristic of this long-acting disinfectant is that a fortified disinfectant of 2,4,4'-trichloro-2'-amino hydroxy diphenyl ether can be produced by adding amino-emulsified silica resin and 1,2 propanediol and fatty alcohol polyethenoxy ether in 2,4,4'-trichloro-2'-hydroxy diphenyl ether.

The long-acting disinfectant obtained has high degree of bacteriostasis, long-acting effect, anti-repeated-pollution, safety and non-toxic. Apparently HD244's bacteriostasis and long-acting features have been improved, and solving, the problem, of eliminating germs on circulating bank notes and other paper products. This long-acting disinfectant possesses bacterioscasis and disinfecting effect against 36 kinds of general bacteria including colibacillus, auratus staphylococcus, white monilia, gonorrhea diplococcus, tubercle bacillus etc. Bacteriostasis and disinfection on surface can still be 66% effective after it's been naturally stored for two years.

Its can use is as follows:

Spray 0.5~1.3 wt % disinfectant solution on the surface of bank notes or other papers, or dip bank notes or other paper into 0.5~1.3 wt % disinfectant solution. After dried by air drying or electrical heating at constant temperature, the surface of circulation bank notes or other paper can be 1~3 years long-acting bacteriostasis effective, especially for solving the problem of bacteria pollution of highly circulating bank notes.

Specific descriptions of the invention with embodiments are as follows:

EXAMPLE 1

This is a kind of long-acting disinfectant. Its ingredients include: 2,4,4'-trichloro-2'-hydroxy diphenyl ether, amino emulsified-silica resin, 1,2 propanediol, fatty alcohol polyethenoxy ether and distilled water. Their weight proportions are as follows:

| | |
|---|---|
| 2,4,4'-trichloro-2'-hydroxy diphenyl ether | 40 parts |
| Amino emulsified-silica resin | 4 parts |
| 1,2 propanediol | 30 parts |
| Fatty alcohol polyethenoxy ether | 10 parts |
| Distilled water | 15 parts |

Preparation method is as follows:

First, mix industrial fatty alcohol polyethenoxy ether, with 1,2 propanediol and aseptic distilled water in weight proportion of 1:0. 8:2, put them into homogeneous reaction oven, stir 3 minutes at the speed of 19,000 r.p.m. at the temperature of 38° C. Then add 40% 2,4,4'-trichloro-2'- hydroxy diphenyl ether, adjust the speed of homogenizer at 800 r.p.m., the temperature in the reaction still is 56° C., stir 4 minutes till all mixture are fused. After the temperature falls to 20° C., add 4% silica resin emulsion whose commodity name is TSA-202. After string 2 minutes at the speed of 200 r.p.m, long-acting disinfectant can be obtained.

EXAMPLE 2

This is a kind of long-acting disinfectant, its ingredients include: 2,4,4'-trichloro-2'-hydroxy diphenyl ether, amino emulsified-silica resin, 1,2 propanediol, fatty alcohol polyethenoxy ether and distilled water, their weight proportion is as follows:

| | |
|---|---|
| 2,4,4'-trichloro-2'-hydroxy diphenyl ether | 50 parts |
| Amino emulsified-silica resin | 3 parts |
| 1,2 propanediol | 20 parts |
| Fatty alcohol polyethenoxy ether | 15 parts |
| Distilled water | 15 parts |

Preparation method is as follows:

According to the method of Example, to produce the long-acting disinfectant, dilute the disinfectant with sterile distilled water to make its concentration to 1.2%. When using, spray it onto the surface of circulating bank notes evenly. After air drying or electrical drying, infecting the surface of the bank notes with the bacteria fluid of auratus staphylococcus, white monilia, gonorrhea diplococcus, tubercle bacillus etc. 36 kinds of common bacteria. In accordance with procedure described in Appendix B of GB15979-1995. The rate of disinfection on bank notes or paper surface is 99.9%. After repeated polluting then washing for over 100 times, the rate of disinfection on the surface can reach over 50%, and the rate of disinfection on the surface can still be up to 66% after the test sample has been stored naturally for two years.

EXAMPLE 3

This is a kind of long-acting disinfectant. Its ingredients include: 2,4,4'-trichloro-2'-hydroxy diphenyl ether, amino emulsified-silica resin, 1,2 propanediol, fatty alcohol polyethenoxy ether and distilled water, their weight proportion is as follows:

| | |
|---|---|
| 2,4,4'-trichloro-2'-hydroxy diphenyl ether | 30 parts |
| Amino emulsified-silica resin | 3 parts |
| 1,2 propanediol | 25 parts |
| Fatty alcohol polyethenoxy ether | 10 parts |
| Distilled water | 40 parts |

When preparing, dilute the long-acting disinfectant, obtained according to the method of Example 1 to the concentration of 0.8% by adding sterile distilled water. At the time the disinfectant is being taken use, make the food packing paper or cartons to be sprayed with, or carton to be dried naturally by air drying or heating. Thus, the long-acting disinfecting and hygiene treatment is carried out.

The disinfecting rate on the test sample of food packing paper or carton can be up to 99.98%, when the test is done according to the method described in Addendix B of the standard GB15979-1955. After the test sample is repeated polluted then washed, for over 100 times, the disinfecting rate on the surface of the sample can even reach over 50%.

Toxic effects test of $LD_{50}$ and skin irritant test with the long-acting disinfectant shows that, the disinfectant possesses excellent property of bacteriostasis, long-acting effect, repeated-pollution resistant, as well as safety and non-poison.

What is claimed is:

1. A long-acting disinfectant, comprising: 2,4,4'-tricholro-2'-hydroxy diphenyl ether, amino emulsified-silica resin, 1,2 propanediol, fatty alcohol polyethenoxy ether and distilled water, in the following proportions by weight:

| | |
|---|---|
| 2,4,4'-trichloro-2'-hydroxy diphenyl ether | 20 to about 50 parts |
| Amino emulsified-silica resin | 3 to about 10 parts |
| 1,2 propanediol | 20 to about 30 parts |
| Fatty alcohol polyethenoxy ether | 10 to about 30 parts |
| Distilled water | 10 to about 40 parts. |

2. A long-acting disinfectant as recited in claim 1, wherein the distilled water is aseptic.

3. A long-acting disinfectant as recited in claim 1, wherein the fatty alcohol polyethenoxy ether is mixed with the distilled water at a proportion ratio of 1:1, then mixed at 11,000 to about 19,000 r.p.m. in a high speed homogenizer for 1 to about 3 minutes, then added 2,4,4'-trichloro-2'-hydroxy diphenyl ether, and the speed of the homogenizer is reduced to 700 to about 900 r.p.m., mixed 3 to about 5 minutes at 50 to about 70° C. until all substances are fused; the temperature is reduced to 15° C. to about 25° C., then amino emulsified-silica resin is added, then mixed 2 to about 6 minutes at 200 to about 500 r.p.m.

4. A long-acting disinfectant as recited in claim 1, said disinfectant is diluted to 0.5~1.3 Wt % aqueous solution with aseptic distilled water to obtain a long-acting disinfectant used for surface disinfecting treatment of circulating bank notes or other paper materials.

* * * * *